US00PP34324P2

(12) United States Plant Patent
Dirr

(10) Patent No.: US PP34,324 P2
(45) Date of Patent: Jun. 14, 2022

(54) ***SPIRAEA* PLANT NAMED 'MAD-SP1'**

(50) Latin Name: *Spiraea japonica*
Varietal Denomination: MAD-SP1

(71) Applicant: University of Georgia Research Foundation, Inc., Athens, GA (US)

(72) Inventor: Matthew A. Dirr, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 17/371,042

(22) Filed: Jul. 8, 2021

(51) Int. Cl.
*A01H 6/74* (2018.01)
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Thomas Horstemeyer, LLP

(57) ABSTRACT

A new and distinct cultivar of *Spiraea* plant named 'MAD-SP1', characterized by a combination of deep pink, self-cleaning flowers with medium green colored foliage, a moderately vigorous growth rate with a compact, low-mounding growth habit, and superior leaf spot resistance.

4 Drawing Sheets

Figure 1:
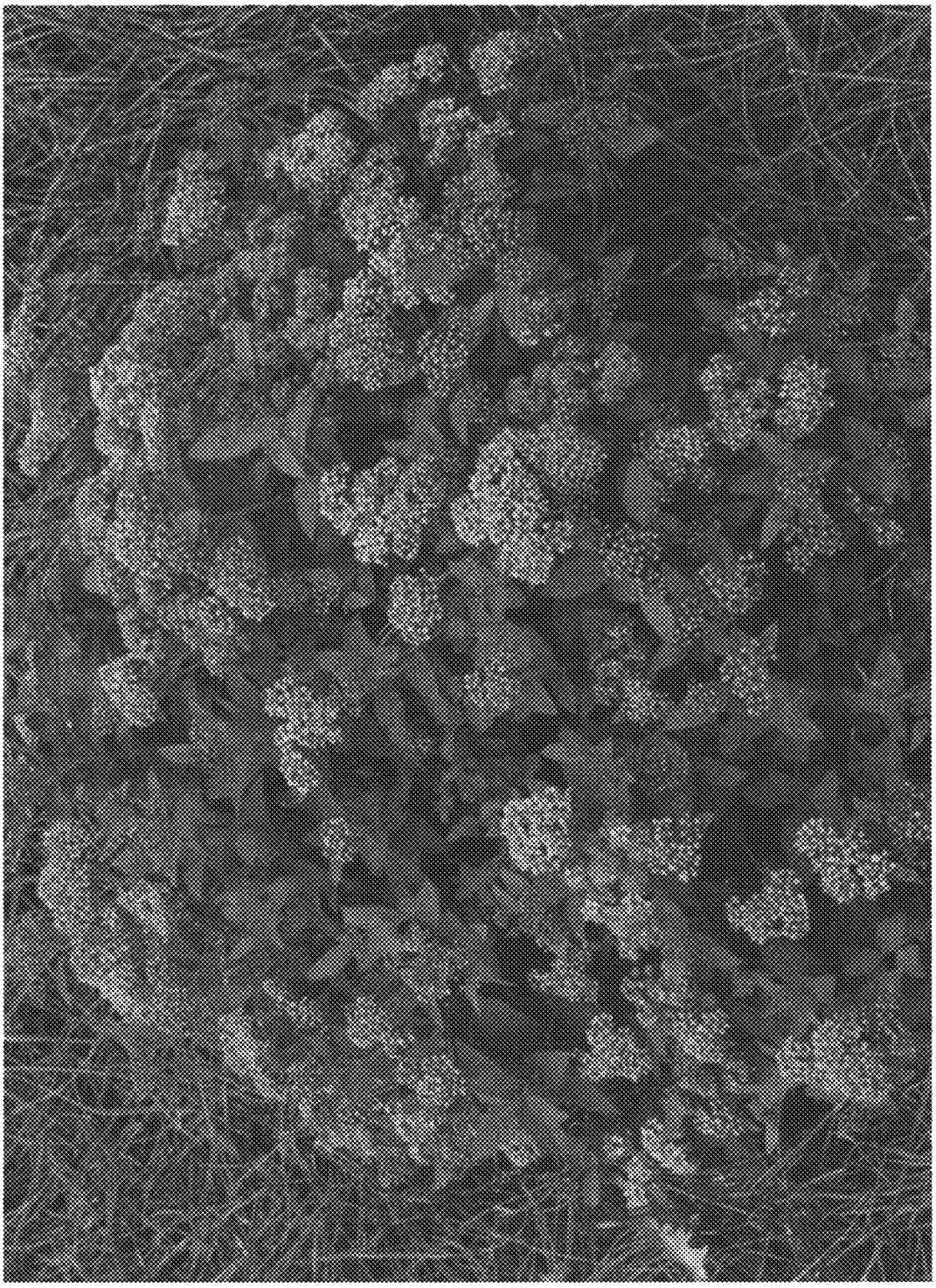

Botanical designation: *Spiraea japonica.*
Cultivar denomination 'MAD-SP1'.

BACKGROUND OF THE INVENTION

The present invention relates to a new and distinct cultivar of *Spiraea*, botanically know as *Spiraea japonica*, and hereinafter referred to by the cultivar name 'MAD-SP1'.

The new *Spiraea japonica* 'MAD-SP1' is a product of a planned *Spiraea* variety trial program conducted by the inventors at a horticulture farm in Athens, Ga. The objective of the *Spiraea* breeding strategy is to create new plant cultivars with abundant numbers of inflorescence, brighter and more vibrant flower colors, compact growth habit and potential leaf spot resistance. These and other qualities are enumerated herein.

The new *Spiraea japonica* 'MAD-SP1' is a product of open pollination method on the mother plant, *Spiraea japonica* 'Little Princess' (patent status unknown) in Athens, Ga., and seed was collected in the fall of 2014. The collected seed was planted in late 2014. In 2015, out of several hundred seedlings that were produced, nine initial seedlings were selected based on compact growth habit, flower color, foliage color, and resistance to leaf scorch and leaf spot. In 2020, two of the 9 seedlings were deemed superior and were selected, the pink flowering new *Spiraea* 'MAD-SP1' and the white flowering *Spiraea* 'MAD-SP2'.

Asexual reproduction of the new *Spiraea japonica* 'MAD-SP1' using softwood cuttings was first accomplished by the inventor in the summer of 2015 at a horticulture farm in Athens, Ga., and has been continued in Athens, Ga. (Zone 7b) since 2015. Observations of the resulting 'MAD-SP1' progeny have shown that the unique features of this new *Spiraea japonica* 'MAD-SP1' are stable and reproduced true to type in successive generations.

SUMMARY OF THE INVENTION

The new *Spiraea* cultivar 'MAD-SP1' has not been observed under all possible environmental conditions. The phenotype may vary somewhat with variations in environment and cultural practices such as temperature, water and fertility levels, soil types, light intensity, and day length without, however, any variance in genotype.

The following traits have been repeatedly observed and are determined to be the unique and distinguishing characteristics of the new *Spiraea japonica* cultivar named 'MAD-SP1'. In combination, these traits set 'MAD-SP1' apart from all other existing varieties of *Spiraea japonica* known to the inventors.

1. Deeper, more vibrant pink colored flowers that are self-cleaning.
2. Medium green colored foliage.
3. Moderately vigorous, compact, low-mounding growth habit
4. Leaf spot resistance Of the many commercially available *Spiraea* cultivars, the most similar in comparison is the female parent, *Spiraea japonica* 'Little Princess'; however, in side by side comparisons, plants of the new cultivar differ from other pink flowering varieties such as *Spiraea* 'Little Princess' primarily by having deeper pink flowers, a more compact growth habit, and superior leaf spot resistance. In 5 years of observation, 'MAD-SP1' has maintained a 3 ft.×3 ft. growth habit, while 'Little Princess' can get up to 6 ft. 'MAD-SP1' has been able to maintain its deeper pink flowers longer than other pink flowering *Spiraeas*, and, thus far, it has shown superior leaf spot resistance.

BRIEF DESCRIPTION OF THE PHOTOGRAPHS

The accompanying colored photographic illustrations show the overall appearance and distinct characteristics of the new cultivar of *Spiraea japonica* 'MAD-SP1' showing the colors as true as possible. Colors in the photographs may differ slightly from the color values cited in the detailed botanical description, which accurately describes the colors of the new *Spiraea japonica* 'MAD-SP1'. The photographs were taken of plants grown outdoors in Watkinsville, Ga. on May 21, 2021.

The photograph labeled FIG. 1 depicts a top-view of a typical two-year-old 'MAD-SP1' plant showing the substantially compact, low-mounding, growth habit, as well as the deeper, vibrant pink colored flowers and medium green foliage.

Figure 2:
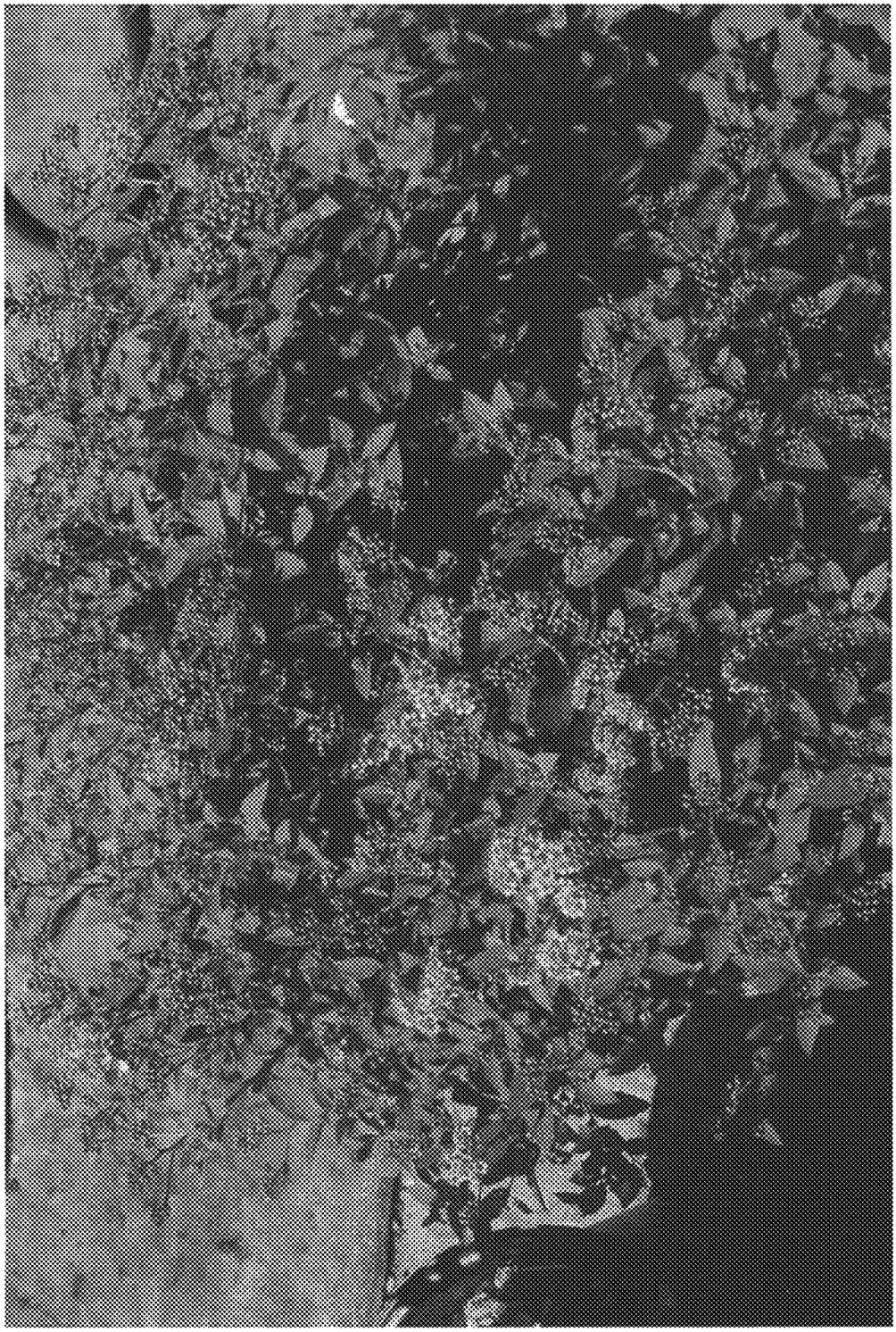

The photograph labeled FIG. 2 depicts another top-view of a typical two-year-old 'MAD-SP1' plant showing the vibrant pink colored flowers and less compact growth habit.

Figure 3:
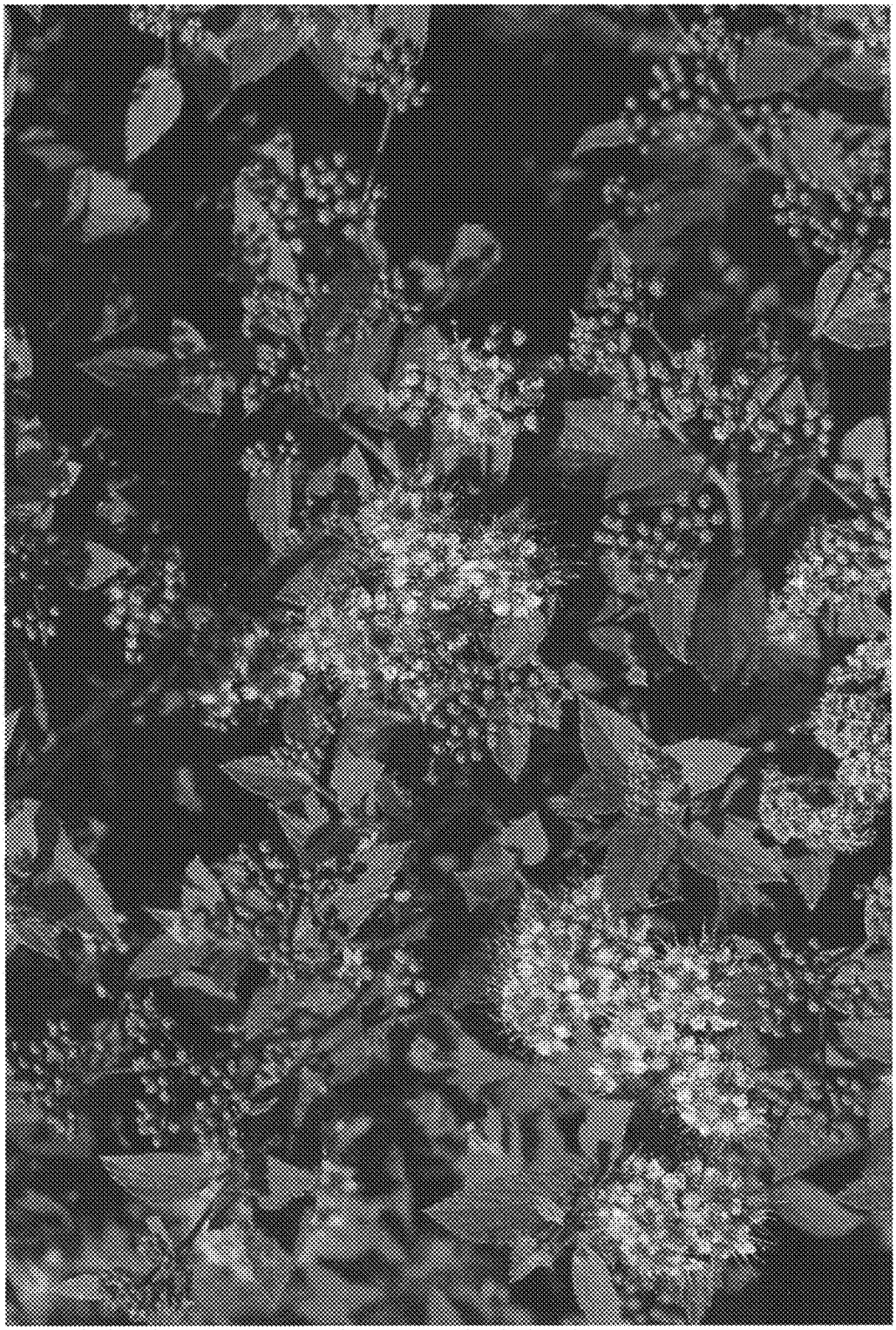

The photograph labeled FIG. 3 depicts a close-up view of a typical two-year-old 'MAD-SP1' plant showing the vibrant pink colored flowers and medium green foliage.

Figure 4:
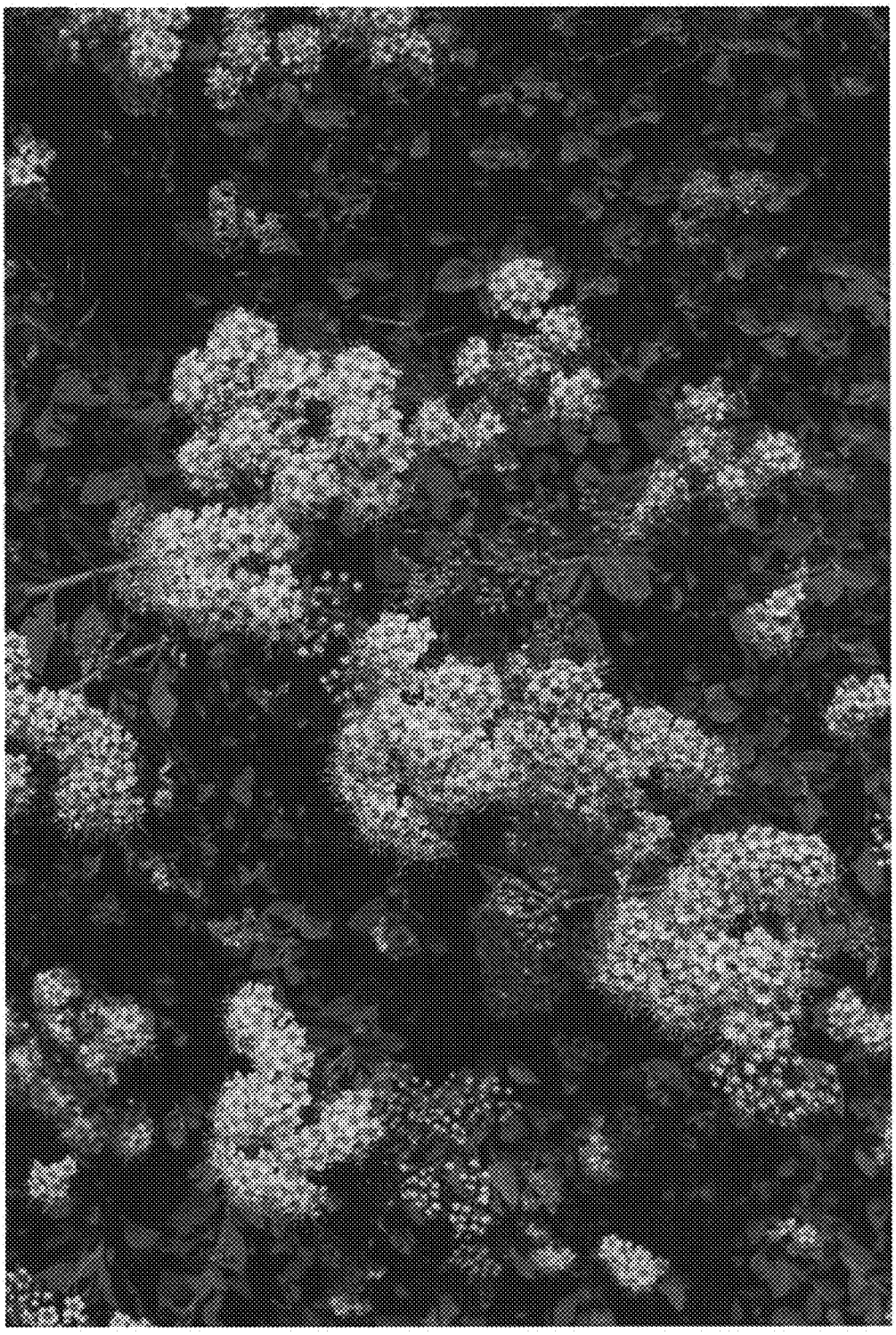

The photograph labeled FIG. 4 depicts on overhead view of a typical two-year-old *Spiraea* 'little princess' plant for comparison, showing the much lighter pink flowers and medium green foliage.

DETAILED BOTANICAL DESCRIPTION

The following traits have been consistently observed in the original plant of this new variety and in asexually propagated progeny grown from Athens, Ga. (Zone 7(b)), and, to the best knowledge of the inventors, their combination forms the unique characteristics of the new variety 'MAD-SP1'.

Throughout this specification, color names beginning with a small letter signify that the name of that color, as used in common speech, is aptly descriptive. Color names beginning with a capital letter designate values based upon The R.H.S. Colour Chart, 5$^{th}$ edition published by The Royal Horticultural Society, London, England in 2015, except where general terms of ordinary dictionary significance are used.

The aforementioned photographs and following observations, measurements, and values describe plants of the *Spiraea japonica* cultivar named 'MAD-SP1'. Data were collected from a horticulture farm and nursery in Athens, Ga. from 2-year-old plants (from cuttings from stock plants and grown in 3-gallon containers in a green house in Athens, Ga. The average low temperatures ranged from about 33-42° in the winter and the average high temperatures ranged from about 85-92° F. in summer.

Botanical classification: *Spiraea japonica* 'MAD-SP1'.

Commercial classification: Ornamental shrub.

Parentage: Open pollination of female parent *Spiraea japonica* 'Little Princess'.

Growth and propagation:

*Propagation type*.—Terminal cutting.

*Growth rate*.—About 10-14 days to initiate roots; about 21 days to produce rooted cutting; Commercial crop time — about 15 weeks from rooted cutting to finish in a 3-gallon container.

*Root description*.—Fibrous and fine, white to brown in color.

*Rooting habit*.—Freely branched, dense.

Plant description:

*Form*.—Compact, low-mounding growth habit.

*Branching habit*.—Freely branching.

*Usage*.—Various uses, such as container patio plants, potted plants, border, hedge, and mass planting.

*Vigor*.—Moderately vigorous.

*Size of plant*.—A. Height (cm): from soil level to top of plant, about 36 cm. B. Plant diameter/area of spread (diameter of the canopy): about 32 cm.

*Branch/stem*.—A. Quantity: about 15 main stems per plant with approximately 10 lateral branches per stem. B. Length: About 22 cm. C. Base Diameter: About 3 mm. D. Aspect: erect to about 45° from center. E: Odor (of bruised stem): F. Internode length: central internode about 11 mm. G: Texture of mature stem: woody. H: Color (R.H.S.): 1. young stem: 145A. 2. mature stem: 200A. I. Shape: upright. J: Strength of lateral branches: strong.

*Leaf*.—A. Leaf type: simple. B. Mature size (L×W): About 4-5 cm×about 2-3 cm. C. Arrangement on stem: alternate. D. Aspect: about 45°. E. Color (R.H.S.): 1. young foliage: upper surface — 143B, venation 151 A; lower surface — 142C, venation 143D. 2. mature foliage: upper surface — 137B, venation 151 A; lower surface — 136C, venation 151A. F. Leaf Number: Average of about 45 per stem. G. Apex: acute. H. Base: cunueate. I. Margin: serrate. J. Shape: ovate. K. Venation: pinnate. L. Texture of upper surface: glabrous, moderately rugose. M. Texture of lower surface: glabrous, ribbed. N. Odor when crushed: none detected.

*Petiole*.—A. Length: About 3 mm. B. Shape: globose. C. Color (R.H.S.): upper and lower surface, 151A. D. Texture: glabrous. E. Diameter: About 1 mm. F. Sheath: unknown.

*Inflorescence(s)*.—A. Type: compound corymbs. B. Number per Plant: about 30-32. C. Size: height — about 2-3 cm; diameter — about 8-10 cm. D. Color (R.H.S.) at full bloom: NN155D. E. Longevity: about 20 days. F. Peduncle. 1. Length: about 1 cm. 2. Diameter: about 2 cm. 3. Color (R.H.S.): 59C. 4. Texture: glabrous. 5. Strength: strong. 6. Aspect: erect to about 45 degrees from branch to axis. 7. Shape: rounded.

*Flower*.—A. Number per Inflorescence: about 200-220. B. Type: single/rotate not persistent. C. Shape: whorl. D. Size (corolla): diameter — about 5 mm; depth — about 3 mm. E. Aspect: upright. F. Color at peak bloom (R.H.S.): 74B. G. Fragrance: none detected. H. Time of full maturity: May. I. Time range for showiness: flowers emerge in May in zone 7b and persist until mid-October. J. Bud (just before opening): 1. Diameter: about 2 mm. 2. Shape: globose. 3. Color (R.H.S.): 74B. 4. Longevity: currently unknown. K. Petals: 1. Number: 5. 2. Size (l×w): about 3 mm×about 3 mm. 3. Shape: orbicular. 4. Apex: rounded. 5. Base: obtuse. 6. Margin: entire. 7. Color when fully opened (R.H.S.): upper and lower surfaces — 74B. 8. Texture: upper and lower surface — glabrous. 9. Arrangement: single whorl. L. Pedicels: 1. Color (R.H.S.): 143B. 2. Texture/Pubescence: glabrous. 3. Length: about 5 mm. 4. Diameter: about 1 mm. 5. Aspect: erect. 6. Strength: strong. M. Sepal(s): 1. Number: 5. 2. Size (l×w): about 3 mm×3 mm. 3. Shape: lanceolate. 4. Apex: acute. 5. Base: fused. 6. Margin: entire. 7. Texture: upper and lower surface — glabrous. 8. Arrangement: single whorl. 9. Color at peak of bloom (R.H.S.): a. Upper surface: N66A. b. Lower surfaces: N66A. N. Calyx: 1. Shape: star shaped. 2. Diameter: about 4 mm. 3. Depth: about 4 mm. O. Male reproductive structures (Androecium): 1. Stamen. a. Number: about 40 per flower. b. Length: about 5 mm. 2. Anther: a. Length: less than about 1 mm. b. Shape: globose. c. Color (R.H.S.): 162A. d. Texture/pubescence: pubescent. 3. Filament: a. Length: about 5 mm. b. Color (R.H.S.): 74B. 4. Pollen: a. Quantity: slight. b. Pollen color (R.H.S.): 162A. P. Female Reproductive structures (Gynoecium): 1. Pistil: a. Length: about 2 mm. b. Pubescence: yes. 2. Stigma: a. Shape: garrated. b. Color (R.H.S.): N15D. c. Pubescence: yes 3. Style: a. Length: about 2 mm b. Number: 5 styles fused to 1 ovary c. Color (R.H.S.): 74B d. Pubescence: yes. 4. Ovary: a. Length: about 0.5 mm. b. Color (R.H.S.): N144B. c. Pubescence: yes.

*Fruit*.—None observed.

*Seed*.—None observed.

Weather/temperature tolerance: Plants of the new *Spiraea* have been observed to regularly tolerate temps as high as 38° C./100° F. in the summer. Conversely it can regularly tolerate −30° F. in the winter. USDA Zone range 4-9.

Disease/pest resistance: To date, plants of the new *Spiraea* have been observed to have the most leaf spot resistance of any *Spiraea* cultivar observed.

It is claimed:

1. A new and distinct cultivar of the *Spiraea* plant named 'MAD-SP1' as illustrated and described herein.

* * * * *

Comparison cultivar *Spiraea* 'little princess'